United States Patent [19]

Mahood et al.

[11] Patent Number: 5,786,497
[45] Date of Patent: Jul. 28, 1998

[54] PROCESS FOR THE PREPARATION OF PHOSPHITES

[75] Inventors: James A. Mahood, Morgantown; Matthew S. Scott, Reedsville, both of W. Va.

[73] Assignee: General Electric Company, Pittsfield, Mass.

[21] Appl. No.: 920,961

[22] Filed: Aug. 29, 1997

[51] Int. Cl.[6] .................................................. C07F 9/145
[52] U.S. Cl. .................................................. 558/85; 558/96
[58] Field of Search .................................................. 558/85, 96

[56] References Cited

U.S. PATENT DOCUMENTS

| | | |
|---|---|---|
| 3,039,993 | 6/1962 | Friedman . |
| 3,056,823 | 10/1962 | Hechenbleikner . |
| 3,281,381 | 10/1966 | Hechenbleikner . |
| 3,305,526 | 2/1967 | Guttag . |
| 3,342,767 | 9/1967 | Buckley . |
| 3,415,906 | 12/1968 | Shepard et al. . |
| 3,441,633 | 4/1969 | Friedman . |
| 3,467,733 | 9/1969 | Dever . |
| 3,482,002 | 12/1969 | Dever . |
| 3,488,407 | 1/1970 | Schall . |
| 3,558,554 | 1/1971 | Kuriyama . |
| 3,845,168 | 10/1974 | Guttag . |
| 4,024,049 | 5/1977 | Shell et al. . |
| 4,067,903 | 1/1978 | Hoch et al. . |
| 4,086,304 | 4/1978 | Hutton et al. . |
| 4,196,117 | 4/1980 | Spivack . |
| 4,276,233 | 6/1981 | Markezich et al. . |
| 4,312,818 | 1/1982 | Maul et al. . |
| 4,322,530 | 3/1982 | Jachimowicz . |
| 4,391,761 | 7/1983 | Block et al. . |
| 4,407,765 | 10/1983 | Hardy . |
| 4,440,696 | 4/1984 | Maul et al. . |
| 4,492,661 | 1/1985 | Maul et al. . |
| 4,656,302 | 4/1987 | Dressler . |
| 4,705,879 | 11/1987 | Dressler . |
| 4,724,056 | 2/1988 | Doane . |
| 4,786,329 | 11/1988 | Chang et al. . |
| 4,882,374 | 11/1989 | Wang et al. . |
| 4,894,481 | 1/1990 | Burt . |
| 5,126,475 | 6/1992 | Bahrmann et al. . |
| 5,235,086 | 8/1993 | Maul et al. . |
| 5,254,709 | 10/1993 | Hunter . |
| 5,371,263 | 12/1994 | Quotschalla et al. . |
| 5,424,348 | 6/1995 | Mahood . |
| 5,438,086 | 8/1995 | Stevenson et al. . |
| 5,468,895 | 11/1995 | Mahood . |
| 5,534,645 | 7/1996 | Quotschalla et al. . |

*Primary Examiner*—Michael G. Ambrose

[57] ABSTRACT

A process for producing organo-phosphites is described that involves heating a di-substituted phosphorohalidite, a phenolic compound, and a polymeric amine. An especially useful polymeric amine is N,N,N'N'-tetraethyl-1,3-propanediamine. Conversions in excess of about 97% are obtained.

17 Claims, No Drawings

PROCESS FOR THE PREPARATION OF PHOSPHITES

FIELD OF THE INVENTION

This invention relates to a process for the preparation of organic phosphites, specifically hindered phosphites. In an especially preferred embodiment, this invention relates to a process to prepare (2,4,6-tri-tertbutylphenyl)(2-butyl-2-ethyl-1,3-propanediol) phosphite.

BACKGROUND OF THE INVENTION

Organic phosphites are used in the stabilization of a wide variety of polymeric systems. Many different phosphites have been proposed for use either alone or in combination with other stabilizers. Such phosphites and their utilities are described in U.S. Pat. Nos. 4,371,647, 4,656,302, 4,705,879, 5,126,475, 5,141,975, and 5,438,086. The importance of organic phosphites as stabilizers has lead to the development of a variety of specialty organic phosphites that have enhanced effectiveness for stabilization.

Sterically hindered organic phosphites, and in particular phosphites containing 2,4,6-substituted phenyl groups wherein the substitution is selected from the group consisting of t-butyl, t-amyl, t-hexyl, cyclohexyl, t-pentyl, and t-octyl, are especially desirable compounds due to their enhanced hydrolytic stability, ease of handling and compatibility with a wide variety of polymeric systems. Mixed alkyl aryl phosphites wherein at least one of the aryl group is one of the aforementioned sterically hindered phenyl groups are also especially preferred for their improved hydrolytic stability over other alkyl substituted phosphites as well as their enhanced compatibility with some polymeric resins, especially polyolefins.

The organic phosphites are generally prepared using methods involving reactions between hydroxyl-substituted alkyl and hydroxyl-substituted aryl compounds and phosphorous trihalides, e.g., phosphorous trichloride. Such methods are described in U.S. Pat. Nos. 4,237,075, 4,440,696, 4,492,661, and 5,235,086. The ease of substitution of the halides on the phosphorous trihalide decreases as each halide is replaced. For example, in the preparation of neoalkyl aryl phosphites, the neoalkyl diol readily reacts in essentially quantitative conversion with a phosphorous trihalide to yield a disubstituted neoalkyl halo phosphite (i.e., an intermediate di-substituted phosphorohalidite). The displacement of the third halo group is less than quantitative and is considerably slower in rate. Additionally, displacement of the third halo group by a sterically hindered phenol is even more difficult and requires elevated temperatures and/or use of a catalyst.

In order to increase the rate of reaction and the degree of completion for displacing the third halide with a sterically hindered moiety, various techniques have been utilized to remove the hydrogen halide by-product from the reaction scheme. These techniques include: use of hydrogen halide acceptors, e.g., amines, and removal of the hydrogen halide with vacuum. Such techniques are described in U.S. Pat. Nos. 3,281,506, 4,237,075, 4,312,818, 4,440,696, and 4,894,481.

Generally the procedures of the prior art result in product conversions of less than about 94%. The resulting phosphite mixture containing a halo-phosphite is extremely difficult to purify and the residual halo-phosphite can lead to acid impurities that affect the long term stability of the desired organic phosphite. It is therefore apparent that a need continues to exist for improved processes for the preparation of organic phosphites, and especially sterically hindered organic phosphites, that overcome the aforementioned difficulties.

SUMMARY OF THE INVENTION

The present invention relates to a new process for the production of organic phosphites from di-substituted phosphites and hydroxyl-containing compounds, preferably sterically hindered phenols, in the presence of a polymeric amine.

In a first embodiment of the present invention, the polymeric amine is an amine of the general formula:

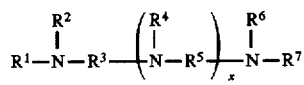

wherein each $R^1$, $R^2$, $R^3$, $R^4$, $R^5$, $R^6$, and $R^7$ is independently a $C_{1-20}$ alkyl, aryl, or alkaryl moiety, and x is an integer of from 0 to about 100.

In a second embodiment of the present invention, the polymeric amine is an amine of the general formula:

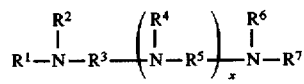

wherein each $R^1$, $R^2$, $R^4$, $R^6$, and $R^7$ is independently a $C_{1-4}$ alkyl moiety, each $R^3$ and $R^5$ is independently a $C_{1-8}$ alkyl moiety, and x is an integer of from 0 to about 5.

In a third embodiment of the present invention, the polymeric amine is an amine of the general formula:

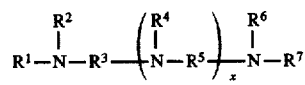

wherein each $R^1$, $R^2$, $R^4$, $R^6$, and $R^7$ is independently a methyl or ethyl moiety, each $R^3$ and $R^5$ is independently a $C_{2-6}$ alkyl moiety, and x is an integer of from 0 to about 2.

In a fourth embodiment of the present invention, the polymeric amine is an amine of the general formula:

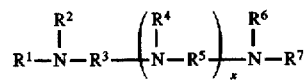

wherein each $R^1$, $R^2$, $R^6$, and $R^7$ is independently a methyl or ethyl moiety, $R^3$ is a $C_{2-6}$ alkyl moiety, and x is 0.

In a fifth embodiment of the present invention, the polymeric amine is an amine of the general formula:

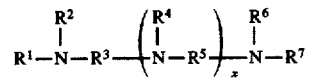

wherein each $R^1$, $R^2$, $R^6$, and $R^7$ is independently a methyl or ethyl moiety, $R^3$ is a $C_{2-4}$ alkyl moiety, and x is 0.

In a sixth embodiment of the present invention, di-substituted phosphite is a di-substituted phosphorohalidite of the general formula:

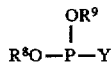

wherein each of $R^8$ and $R^9$ is independently a $C_{1-20}$ alkyl, aryl, or alkaryl moiety and Y is a halogen or other good leaving group. It is also possible for $R^8$ and $R^9$ to be interconnected (i.e., the residual of a diol) such that the resultant di-substituted phosphite contains a cyclic phosphite of the general formula:

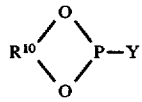

wherein $R^{10}$ is $C_{1-20}$ alkyl, aryl, or alkaryl moiety and Y is a halogen or other good leaving group.

In a seventh embodiment of the present invention, the hydroxyl-containing compound is a phenol of the general formula:

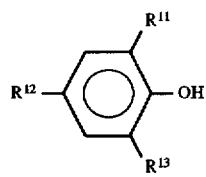

wherein each $R^{11}$, $R^{12}$ and $R^{13}$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

In a eighth embodiment of the present invention, the hydroxyl-containing compound is a phenol of the general formula:

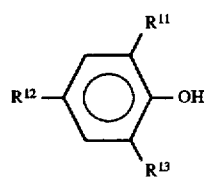

wherein each $R^{11}$, $R^{12}$, and $R^{13}$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^{11}$ and $R^{12}$ is t-butyl, t-amyl, t-hexyl, cyclohexyl, cumyl, t-pentyl, or t-octyl.

In a ninth embodiment of the present invention, the polymeric amine is an amine of the general formula:

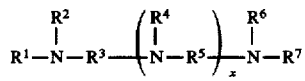

wherein each $R^1$, $R^2$, $R^6$, and $R^7$ is independently a methyl or ethyl moiety, $R^3$ is a $C_3$ alkyl moiety, and x is 0; the di-substituted phosphite is a cyclic phosphite of the general formula:

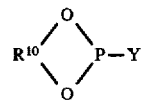

wherein $R^{10}$ is $C_{1-20}$ alkyl, aryl, or alkaryl moiety and Y is a halogen or other good leaving group; and the hydroxyl-containing compound is a phenol of the general formula:

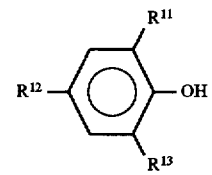

wherein each $R^{11}$, $R^{12}$, and $R^{13}$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^{11}$ and $R^{12}$ is t-butyl, t-amyl, t-hexyl, cyclohexyl, cumyl, t-pentyl, or t-octyl.

In a tenth embodiment of the present invention, the polymeric amine is an amine of the formula:

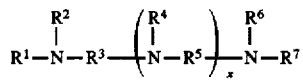

wherein each $R^1$, $R^2$, $R^6$, and $R^7$ is a methyl, $R^3$ is a $C_4$ alkyl moiety, and x is 0; the di-substituted phosphite is a cyclic phosphite of the general formula:

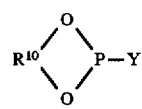

wherein $R^{10}$ is $C_{1-20}$ alkyl, aryl, or alkaryl moiety and Y is a halogen or other good leaving group; and the hydroxyl-containing compound is a phenol of the formula:

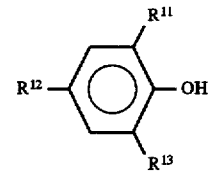

wherein each $R^{11}$, $R^{12}$, and $R^{13}$ is t-butyl.

In an eleventh embodiment of the present invention, the polymeric amine is an amine of the formula:

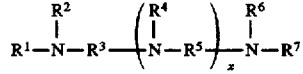

wherein each $R^1$, $R^2$, $R^6$, and $R^7$ is a methyl, $R^3$ is a $C_3$ alkyl moiety, and x is 0; the di-substituted phosphite is a cyclic phosphite of the formula:

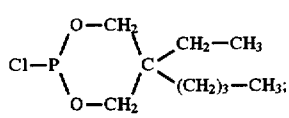

and the hydroxyl-containing compound is a phenol of the formula:

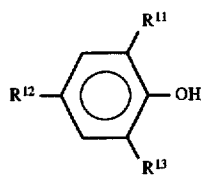

wherein each $R^{11}$, $R^{12}$, and $R^{13}$ is t-butyl.

In an twelfth embodiment of the present invention, the conversion to the organic phosphite is at least about 97%.

These and other embodiments of the present invention will become apparent to those skilled in the art with the disclosure of the present invention.

DETAILED DESCRIPTION OF THE INVENTION

The present invention relates to processes to produce organic phosphites of the general formula $(RO)_3P$ wherein the R groups are independently a $C_{1-20}$ alkyl, aryl, or alkaryl moiety. Organic phosphites are typically produced by reacting a phosphorous trihalide, e.g., phosphorous trichloride, with hydroxyl-containing compounds wherein the halides are displaced on the phosphorous trihalide by the hydroxyl-containing compounds. The ease of substitution by the hydroxyl-containing compounds depends at least partly on the steric bulk of the hydroxyl-containing compounds. When the hydroxyl-containing compound has a low steric demand (i.e. the hydroxyl-containing compound is not a sterically hindered phenol), the displacement of the halides is somewhat statistical. However, as the steric demand of the hydroxyl-containing compound increases, increased selectivity may be obtained to achieve less substituted halophosphites. In displacement of the first two halides on the phosphorous trihalide, the reactions are generally facile and proceed to completion without the need for catalysis regardless of the steric limitations of the hydroxyl-containing compound.

In the displacement of the third halide moiety from the di-substituted phosphorus halide, the degree of conversion to the tri-substituted phosphite is adversely affected by steric considerations of both the di-substituted phosphorus halide and the hydroxyl-containing compound. Catalysts are often employed in the art to increase the degree of conversion to the tri-substituted phosphite. It was quite surprising discovered that the use of polymeric amines in the process to displace the third halide moiety from the di-substituted phosphorus halide results in extremely high conversions to the tri-substituted phosphite.

As previously discussed, the process of the present invention is useful to produce organic phosphites of the general formula $(RO)_3P$ wherein the R groups are independently a $C_{1-20}$ alkyl, aryl, or alkaryl moiety. As the R groups become increasingly sterically hindered, the conversion from the di-substituted phosphorohalidite to the tri-substituted phosphite becomes more difficult and the conversion percentage becomes diminished. General methods to prepare organic phosphites are known in the are and are exemplified by U.S. Pat. Nos. 3,415,906; 3,488,407; 3,467,733; 4,276,233; 4,318,845; and 5,424,348.

The reaction between the hydroxyl-containing compounds and phosphorus trihalide to form an intermediate di-substituted phosphorohalidite may be carried out with or without the use of a solvent. Typically $PCl_3$ is utilized although other phosphorus halides or derivatives may be used. Generally, $PCl_3$ is added to the hydroxyl-containing compounds or alternatively, the hydroxyl-containing compounds can be added to $PCl_3$. Preferably the hydroxyl-containing compounds are added to the $PCl_3$ with the reaction mixture being maintained at a temperature of about 5° to 50° C. The reaction is quite exothermic in the absence of a solvent, but a temperature moderating effect is produced by the cooling effect of vigorous HCl evolution. Hence, by effective control of the addition of hydroxyl-containing compounds, the reaction may be made self-regulating in the temperature range of between about 5° to 15° C. A slower addition favors lower temperatures and it is preferred to cool the reaction mixture during the addition. A slight excess of stoichiometric amounts of $PCl_3$ is commonly utilized.

When a solvent is utilized, it is important that the solvent be neutral to the reaction ingredients and by-products. Typical solvents include, for example, toluene, heptane, xylene, methylene chloride, chloroform, and benzene. Preferred solvents are methylene chloride, heptane, or xylene.

After the reaction has gone to completion, the bulk of the halide by-product, such as HCl, may optionally be removed by gently raising the temperature of the product to room temperature to about 50° C. Any solvent utilized is generally at least partially removed, typically by application of a vacuum, to insure complete removal of the hydrogen halide by-product to yield an intermediate di-substituted phosphorohalidite product.

The intermediate di-substituted phosphorohalidite product is next allowed to react with a hydroxy-substituted compound to yield the desired trisubstituted organic phosphite. The reaction between the intermediate di-substituted phosphorohalidite product and the hydroxy-substituted compound may be conducted in the same reaction vessel that was employed to produce the intermediate phosphorohalidite by merely introducing the hydroxy-substituted compound followed by the polymeric amine into the reactor. Alternatively, the hydroxy-substituted compound and the polymeric amine may be premixed, optionally with heating to aid in dissolution, and the intermediate di-substituted phosphorohalidite added to the mixture. It was unexpectedly found that when the hydroxy-substituted compound and the polymeric amine were premixed before addition of the intermediate di-substituted phosphorohalidite product that less color was formed in the final phosphite product. Additionally, it was unexpectedly found that the color of the final phosphite product could be controlled by the addition rate of the intermediate di-substituted phosphorohalidite product, with a slower addition rate leading to less color in the final phosphite product. An appropriate addition rate can be readily determined by color determination of the final product and depends also on factors such as the exact reaction conditions, ratios of ingredients, and equipment utilized. Regardless of the order of addition, the reaction is generally carried out at a suitable temperature between about 20° to about 175° C. and preferably between about 120° to about 155° C. The pressure of the reaction system is maintained between about 50 millimeters mercury absolute to atmospheric pressure. Typical reaction times to substantial completion are from 1 to about 24 hours. Preferably, the temperature and pressure conditions are selected to afford the maximum amount of product within a time period of about 1 to about 6 hours.

The polymeric amines of the present invention are known compounds and include amines of the general formula:

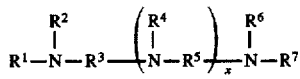

wherein each $R^1$, $R^2$, $R^3$, $R^4$, $R^5$, $R^6$, and $R^7$ is independently a $C_{1-20}$ alkyl, $C_{6-20}$ aryl, or $C_{7-20}$ alkaryl moiety, and x is an integer of from 0 to about 100. In a preferred embodiment, each $R^1$, $R^2$, $R^4$, $R^6$, and $R^7$ is independently a $C_{1-4}$ alkyl moiety, each $R^3$ and $R^5$ is independently a $C_{1-8}$ alkyl moiety, and x is an integer of from 0 to about 5.

The role of the amine in the current process is believed to be two-fold depending in part on the structure of the hydroxyl-containing compound. When the hydroxyl-containing compound is a phenolic compound, the polymeric amine is believed to deprotonate the phenolic compound to result in the formation of a phenoxide. The phenoxide in turn is believed to displace the halide from the phosphorous halide. Additionally, it is believed that the polymeric amine forms an amine salt with the hydrogen halide by-product from the phosphorous halide displacement reaction. It is further believed that when the amine salt has a low solubility in the reaction medium, the displacement reaction is driven to completion and very high conversions to the desired tri-substituted organic phosphite are achieved.

Polymeric amines having relatively short chain lengths are especially preferred in the present invention. As the chain length become longer than about ten carbons, the conversion to the desired tri-substituted organic phosphite becomes diminished. Additionally, aromatic substitution on the polymeric amine can result in an increased color in the tri-substituted organic phosphite, although the conversion to the desired phosphite is quite acceptable. Thus, in an especially preferred embodiment, the polymeric amine is of the formula:

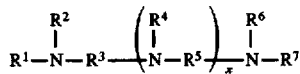

wherein each $R^1$, $R^2$, $R^4$, $R^6$, and $R^7$ is independently a methyl or ethyl moiety, each $R^3$ and $R^5$ is independently a $C_{2-6}$ alkyl moiety, and x is an integer of from 0 to about 2. The most preferred polymeric amines are wherein each $R^1$, $R^2$, $R^6$, and $R^7$ is independently a methyl or ethyl moiety, $R^3$ is a $C_{2-4}$ alkyl moiety, and x is 0. The use of polymeric amines of longer repeating units (i.e., X greater than 2) in the present invention does lead to very high conversions, however, with the disadvantage of generally being too water soluble to provide for easy recycling of the polymeric amine.

Useful polymeric amines include, for example, N,N,N',N'-tetramethyl-1,3-propanediamine; N,N,N',N'-tetraethyl-1,3-propanediamine; N,N,N'-trimethyl-N'-tallow-1,2-propanediamine; N,N,N',N",N"-pentamethyldiethylenetriamine, N,N,N',N'-tetramethyl-1,4-butanediamine; N,N,N',N'-tetramethyl-1,3-butanediamine; N,N,N',N'-tetramethyl-1,6-hexamethylenediamine; N,N,N',N'-tetraethyl-1,4-butanediamine; N,N,N',N'-tetraethyl-1,3-butanediamine; N,N,N',N'-tetraethyl-1,6-hexamethylenediamine; N,N,N',N'-tetraethyl-1,2-ethanediamine; N,N,N',N'-tetramethyl-1,2-ethanediamine; as well as the higher chain homologues and polymers of the foregoing.

In the practice of the present invention, the preferred polymeric amines lead to conversion degrees of at least 97%, preferably of at least 98%. Additionally, the polymeric amines preferably have flash points of at least 100° F. so as to be considered to be combustible from a handling viewpoint. Polymeric amines having flash points of less than 100° F. and are considered to be flammable and as such require explosion-proof equipment in order to be handled safely in a commercial environment.

The preferred polymeric amines also have relatively low vapor pressures in order to minimize evaporation of the polymeric amines. By relatively low vapor pressures is meant vapor pressures of below about 10 mm, preferably below about 3 mm, and most preferably below about 1 mm, when measured at 25° C.

The polymeric amine in the present invention is preferably used in at least about an equimolar amount based upon the nitrogen content of the polymeric amine to the molar amount of halide present on the di-substituted phosphorohalidite. That is, the molar ratio of nitrogen in the polymeric amine to the di-substituted phosphorohalidite is at least 1:1, preferably at least 1.1:1. An unexpected advantage obtained with the use of a polymeric amine instead of a monoamine in the present invention is an increased reactor vessel utilization with the polymeric amine. For example, when the polymeric amine is a diamine, a single mole of diamine affords two equivalents of amine nitrogen. When a monoamine is utilized only a single equivalent of amine nitrogen is obtained per mole of monoamine. Likewise, when the polymeric amine is a triamine, a single mole of triamine affords three equivalents of amine nitrogen. Accordingly, more active sites are present in a given volume of a polymeric amine than with a monoamine and greater reaction vessel utilization can be achieved.

It is during the reaction of the di-substituted phosphorohalidite and the hydroxy-substituted compound that the corresponding ammonium hydrogen chloride salt is formed between the polymeric amine and the hydrogen chloride by-product (chloride is described herein as $PCl_3$ is the most often used starting halophosphite). Another unexpected advantage of using a polymeric amine is that less salt is made in the reaction mixture which also is advantage from a process viewpoint. As previously discussed, it is believed that when the preferred polymeric amines are utilized that the salt formed has diminished solubility in the reaction medium and that this diminished solubility drives the reaction to very high conversions. Therefore, it should be clear that the present invention includes polymeric amines whose hydrogen halide salts have a lower solubility in the phosphite reaction mixture than does the corresponding monoamine salt.

The final proportions of reactants are at least approximately stoichiometric. It is often desirable to work with at least a slight stoichiometric excess of one of the reactants to help drive the reaction as for to completion as possible.

After completion of the reaction, the polymeric amine salt present in the reaction mixture may be removed by the filtration with the salt washed with additional polymeric amine or a solvent in which the salt is not soluble. Typical solvents suitable for this purpose include, for example, hindered alcohols with isopropyl alcohol being preferred.

The reaction product can be dissolved in an inert organic solvent and filtered to remove any solid materials. The solvent can be removed by flash distillation or another solvent removal technique or alternatively, the phosphite product can be isolated by crystallization or precipitation from an inert organic solvent. Typical inert organic solvents include hexane, heptane, octane, toluene, isopropyl alcohol, and the like. The phosphite product can also be purified using melt crystallization techniques or combinations of melt crystallization and solvent crystallization and/or precipitation.

It was unexpectedly found that use of a high boiling hydrocarbon solvent in place of the traditional organic solvents mentioned above offers numerous advantages. By high boiling is meant solvents that begin to boil at about 175° C. or higher. The useful upper limit on the boiling point is determined, at least in part, by the process engineering equipment that is used to remove the trace amount of solvent residue remaining with the phosphite. The useful upper limit should be low enough that the amount of solvent remaining is de minimis after treatment to remove the solvent. The advantages in using a high boiling solvent include: increased concentrations of crude phosphite due to the higher temperature capability, less flammability, reduced solvent loss from evaporation, and less odor from lower vapor pressure. Especially useful high boiling hydrocarbon solvents include those available from Exxon Corporation under the tradename NORPAR. An especially preferred solvent is NORPAR 13.

When the phosphite stabilizer is isolated in crystalline form, the present invention contemplates that it may be utilized in solid amorphous form. The amorphous phosphite composition is formed by rapid cooling of melt of the phosphite. Such melt may be a mixture of the phosphite and polyamine which is rapidly cooled to form a solid amorphous phosphite composition. The amorphous nature of composition enhances the hydrolytic stability of the solid composition compared to crystalline composition containing the same constituents.

The phosphites made by the process of the present invention include all organic phosphites. Especially preferred phosphites, however, are sterically hindered phosphites wherein at least of the organic substituents are of the general formula:

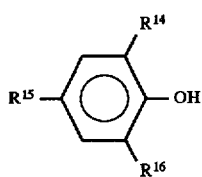

wherein each $R^{14}$ is independently selected from the group consisting of t-butyl, t-amyl, t-hexyl, cyclohexyl, cumyl, t-pentyl, and t-octyl, wherein each $R^{15}$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl, and wherein each $R^{16}$ is independently selected from the group consisting of hydrogen, t-butyl, t-amyl, t-hexyl, cyclohexyl, cumyl, t-pentyl, and t-octyl.

The remaining two substituents on the phosphite (i.e., the substituents present on the di-substituted phosphorohalidite) can be a wide variety of $C_{1-20}$ hydroxy-alkyl, $C_{6-20}$ hydroxy-aryl, or $C_{7-20}$ hydroxy-alkaryl residues. In a preferred embodiment, the remaining two substituents are derived from a diol such that the resultant organic phosphite is a cyclic phosphite. The diol may contain more than two hydroxyl moieties. Useful diols include the following compounds:

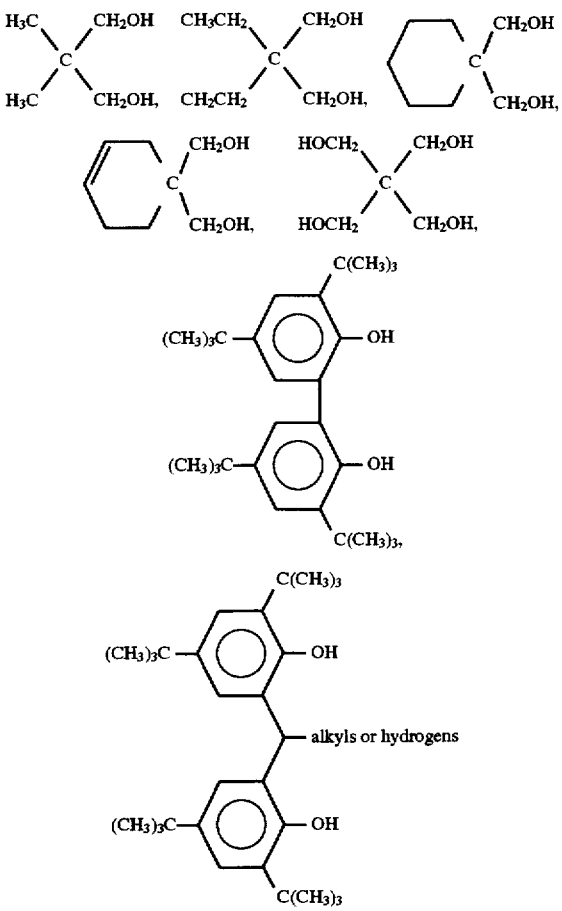

In a preferred embodiment, diols of the general formula:

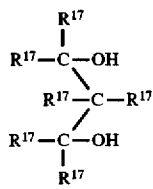

wherein each $R^{17}$ is independently a hydrogen or a $C_{1-10}$ alkyl group are especially preferred. An especially preferred diol is:

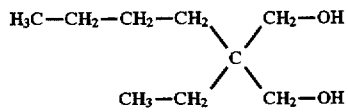

It should be clear that the corresponding di-substituted phosphorohalidite from this diol is 5-butyl-5-ethyl-2-chloro-1,3,2-dioxaphosphorinane.

All patents cited by reference are incorporated herein by reference.

In order that those skilled in the art will be better able to practice the invention, the following examples are given by way of illustration and not by way of limitation.

EXAMPLES

General Procedure

A reaction vessel was charged with 2,4,6-tri-t-butylphenol (1.05 mol) and the amine (1.05 mol) and warmed to about 100° C. under an inert atmosphere. 5-butyl-5-ethyl-2-chloro-1,3,2-dioxaphosphorinane (1.0 mol) having the formula:

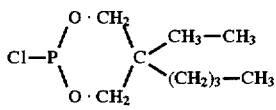

was added and the reaction mixture was maintained at about 120° to 150° C. for about 4 hours. The degree of product conversion to the tri-substituted phosphite was measured by gas chromotagraphy. At the end of the reaction period, the warm reaction mixture was filtered to remove the amine salt and the salt was washed with excess amine. The reaction filtrate was combined with the amine washings and the amine and excess 2,4,6-tri-t-butylphenol was stripped from the solution under vacuum. The final phosphite was crystallized from acetonitrile or isopropyl alcohol. The resultant phosphite had the formula:

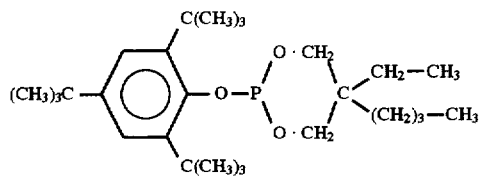

The recovered amine salt was washed with aqueous sodium hydroxide to release the free polymeric amine. Depending on the exact structure of the polymeric amine, heat may be necessary to separate the polymeric amine from the aqueous layer.

The following table provides a comparison between numerous amines in the above process. The amines are abbreviated as follows:

| Amine | chemical name |
|---|---|
| TEEDA | N,N,N',N'-tetraethyl-1,2-ethanediamine |
| TPEDA | N,N,N',N'-tetrapropyl-1,2-ethanediamine |
| TEPDA | N,N,N',N'-tetraethyl-1,3-propanediamine |
| DEDMPA | N,N-diethyl-N',N'-dimethylpropanediamine |
| TMPDA | N,N,N',N'-tetramethyl-1,3-propanediamine |
| TMBDA | N,N,N',N'-tetramethyl-1,4-butanediamine |
| TMHDA | N,N,N',N'-tetramethyl-1,6-hexamethylenediamine |
| TPA | tripropylamine |
| TBA | tributylamine |
| TEA | triethylamine |
| DMDDA | dimethyldodecylamine |
| DMOA | dimethyloctylamine |
| poly-1 | N,N,N',N',N''-pentamethyldiethylenetriamine |
| pyridine | pyridine |

TABLE 1

| Amine | conversion % | flash point, °F. | $VP_{25°C., mm}$ | $BP_{1 atm}$ | recovery |
|---|---|---|---|---|---|
| TEEDA | 97.5 | 138 | 0.8 | 190 | brine |
| TPEDA | 91.2 | | 0.1 | | brine |
| TEPDA | 98.1 | 169 | 0.3 | 205 | water |
| DEDMPA | 98.4 | | 1 | 180 | brine |
| TMPDA | 99.4 | 89 | 10 | 145 | hot brine |
| TMBDA | 96.0 | 115 | 3 | 166 | hot brine |
| TMHDA | 95 | 165 | 0.2 | 210 | n.a. |
| TPA | 92.2 | 98 | 5 | 155 | water |
| TBA | 78.5 | — | — | — | — |

TABLE 1-continued

| Amine | conversion % | flash point, °F. | $VP_{25°C., mm}$ | $BP_{1 atm}$ | recovery |
|---|---|---|---|---|---|
| TEA | 88.0 | — | — | — | — |
| DMDDA | 95.5 | >230 | <0.1 | | water |
| DMOA | 96.2 | 149 | 0.6 | 195 | water |
| poly-1 | 98.4 | 177 | unknown | 201 | n.a. |
| pyridine | 25.1 | — | — | — | — |

As illustrated by the above data, the monoamines (e.g., TBA, pyridine, TPA, DMOA, DMDDA) can in some instances achieve conversions up to about 96%. In contrast, conversions as high as 99.4% have been achieved with the use of a polymeric amine. As previously mentioned, in addition to achieving higher conversions than a monoamine, preferred polymeric amines also have flash points in excess of 100° F. and have limited solubility in water such that they can be readily recycled. An especially preferred polymeric amine is N,N,N'N'-tetraethyl-1,3-propanediamine as having a high conversion, a flash point in excess of 100° F., limited solubility in water, as well as a low vapor pressure to minimize worker exposure.

What is claimed:

1. A process to produce an organic phosphite, wherein said process comprises heating a di-substituted phosphorohalidite with a phenolic compound and a polymeric amine.

2. The process of claim 1, wherein the polymeric amine is an amine of the general formula:

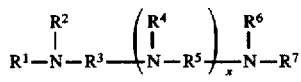

wherein each $R^1$, $R^2$, $R^3$, $R^4$, $R^5$, $R^6$, and $R^7$ is independently a $C_{1-20}$ alkyl, aryl, or alkaryl moiety, and x is an integer of from 0 to about 100.

3. The process of claim 1, wherein the polymeric amine is an amine of the general formula:

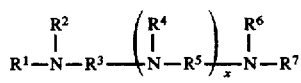

wherein each $R^1$, $R^2$, $R^4$, $R^6$, and $R^7$ is independently a $C_{1-4}$ alkyl moiety, each $R^3$ and $R^5$ is independently a $C_{1-8}$ alkyl moiety, and x is an integer of from 0 to about 5.

4. The process of claim 1, wherein the polymeric amine is an amine of the general formula:

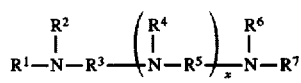

wherein each $R^1$, $R^2$, $R^4$, $R^6$, and $R^7$ is independently a methyl or ethyl moiety, each $R^3$ and $R^5$ is independently a $C_{2-6}$ alkyl moiety, and x is an integer of from 0 to about 2.

5. The process of claim 1, wherein the polymeric amine is an amine of the general formula:

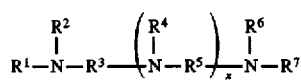

wherein each $R^1$, $R^2$, $R^6$, and $R^7$ is independently a methyl or ethyl moiety, $R^3$ is a $C_{2-6}$ alkyl moiety, and x is 0.

6. The process of claim 1, wherein the polymeric amine is an amine of the general formula:

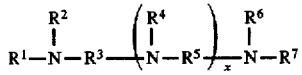

wherein each $R^1$, $R^2$, $R^6$, and $R^7$ is independently a methyl or ethyl moiety, $R^3$ is a $C_{2-4}$ alkyl moiety, and x is 0.

7. The process of claim 1, wherein the phenolic compound is a sterically hindered phenol of the formula

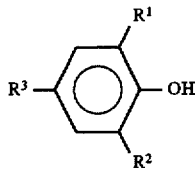

wherein each $R^1$ is independently selected from the group consisting of t-butyl, t-amyl, t-hexyl, cyclohexyl, cumyl, t-pentyl, and t-octyl, wherein each $R^2$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl, and
wherein each $R^3$ is independently selected from the group consisting of hydrogen, t-butyl, t-amyl, t-hexyl, cyclohexyl, cumyl, t-pentyl, and t-octyl.

8. The process of claim 7, wherein $R^1$, $R^2$, and $R^3$ are each t-butyl.

9. The process of claim 1, wherein the di-substituted phosphorohalidite has the general formula:

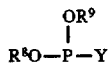

wherein each of $R^8$ and $R^9$ is independently a $C_{1-20}$ alkyl, aryl, or alkaryl moiety and Y is a halogen.

10. The process of claim 1, wherein the di-substituted phosphorohalidite is a cyclic phosphite of the general formula:

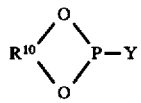

wherein $R^{10}$ is $C_{1-20}$ alkyl, aryl, or alkaryl moiety and Y is a halogen.

11. The process of claim 1, wherein the substituents present on the di-substituted phosphorohalidite are derived from a diol of the general formula:

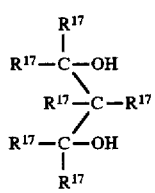

wherein each $R^{17}$ is independently a hydrogen or a $C_{1-10}$ alkyl group.

12. The process of claim 1, wherein the di-substituted phosphorohalidite is 5-butyl-5-ethyl-2-chloro-1,3,2-dioxaphosphorinane.

13. The process of claim 1, wherein the conversion to the organic phosphite is at least about 97%.

14. The process of claim 1, wherein the process further comprises heating the di-substituted phosphorohalidite, the phenolic compound and the polymeric amine in a solvent.

15. The process of claim 1, wherein the polymeric amine is an amine of the formula:

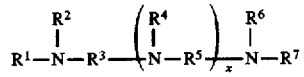

wherein each $R^1$, $R^2$, $R^6$, and $R^7$ is a methyl, $R^3$ is a $C_4$ alkyl moiety, and x is 0; the di-substituted phosphorohalidite is a cyclic phosphite of the formula:

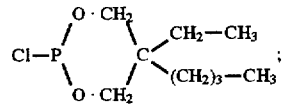

and the phenolic compound is a phenol of the formula:

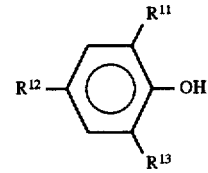

wherein each $R^{11}$, $R^{12}$, and $R^{13}$ is t-butyl.

16. A process for the preparation of a phosphite of the formula:

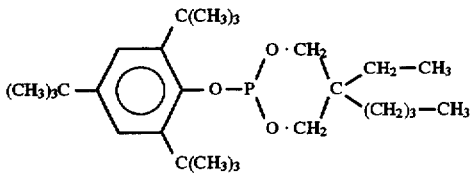

wherein said process comprises heating a polymeric amine of the formula:

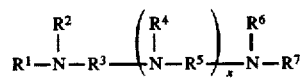

wherein each $R^1$, $R^2$, $R^6$, and $R^7$ is a methyl, $R^3$ is a $C_4$ alkyl moiety, and x is 0; with a phosphorohalidite of the formula:

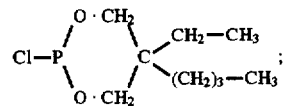

and a phenolic compound of the formula:
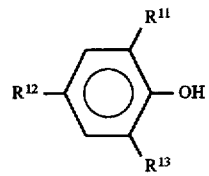
wherein each $R^{11}$, $R^{12}$, and $R^{13}$ is t-butyl.
17. The process of claim 16, wherein the conversion to the phosphite is at least about 97%.
* * * * *